Figure 2:
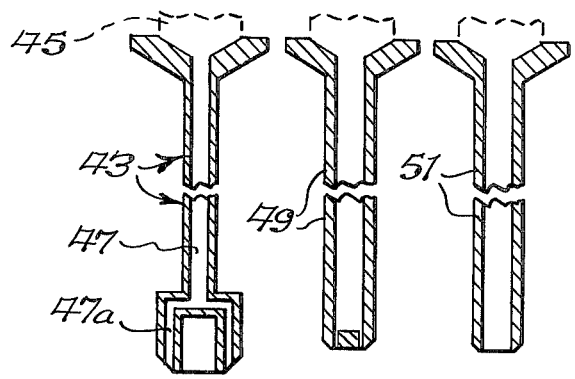

United States Patent [19]

Weyn

[11] 4,098,435
[45] Jul. 4, 1978

[54] STABILIZED DENTRIFICE CONTAINING INITIALLY PHYSICALLY SEPARATED NORMALLY REACTIVE COMPONENTS

[75] Inventor: Hendrik Frans Weyn, Le Chesnay, France

[73] Assignee: Colgate-Palmolive Company, New York, N.Y.

[21] Appl. No.: 714,736

[22] Filed: Aug. 16, 1976

[51] Int. Cl.$^2$ .............................................. B65D 35/22
[52] U.S. Cl. ........................................................ 222/94
[58] Field of Search ........................ 222/94, 107, 145; 424/52, 49; 206/219

[56] References Cited

U.S. PATENT DOCUMENTS

| | | | |
|---|---|---|---|
| 2,982,396 | 5/1961 | Shihadeh | 206/219 |
| 3,002,658 | 10/1961 | Sajda | 222/94 |
| 3,747,804 | 7/1973 | Raaf et al. | 222/94 X |

Primary Examiner—Robert B. Reeves
Assistant Examiner—John P. Shannon
Attorney, Agent, or Firm—Robert L. Stone; Murray M. Grill; Herbert S. Sylvester

[57] ABSTRACT

A stabilized and extrudable paste or gel dentifrice comprises two dentifrice portions, each of which includes a component which is chemically reactive with the other such component in the other portion, with the portions being maintained separate from each other in a dispensing container from which they are dispensable together through a closable opening therein in response to pressure. One of the reactive components is an alkali metal fluorine-containing salt such as sodium fluoride or sodium monofluorophosphate, used for its effect in hardening tooth enamel, and the other is a water insoluble calcium salt, such as dicalcium phosphate, tricalcium phosphate or calcium carbonate, used as a polishing agent. The dentifrice portions are preferably separated by an extrudable material, such as a polyhydric alcohol-water gel of a gum, such as sodium carboxymethyl cellulose. Also within the invention is a method for the manufacture of the mentioned dentifrice.

8 Claims, 3 Drawing Figures

STABILIZED DENTIFRICE CONTAINING INITIALLY PHYSICALLY SEPARATED NORMALLY REACTIVE COMPONENTS

This invention relates to stabilized packaged dentifrices containing normally reactive components. More particularly, it relates to such a dentifrice, with reactive portions packaged so as to be dispensable together but to remain separate during storage before intended use. The invention also includes methods of making such products.

Dentifrice compositions in paste, gel or cream form are well known and are conventionally dispensed from collapsible tubes by applications of compressing finger pressure on the tubes. "Aerosol" or pressure packed dentifrice compositions have been marketed and "squeeze-bottle" containers, usually made of resilient synthetic organic polymeric material, e.g., polyethylene, may be used to dispense dentifrices. The tubes employed in the prior art are usually of aluminum although other metal tubes (which are non-resilient) may also be employed. In the past tin and lead tubes were used but if suitable protective linings, usually of "plastic", are present, various other metals are also useful. Resilient synthetic organic polymeric plastic tubes have been used but have not been as popular as the collapsible metal tubes.

Although most dentifrices are opaque white, in recent years clear gels have been marketed and colored dentifrices have found favor in the marketplace. Striped dentifrices have been produced by any of a variety of filling and dispensing means, usually being made by mixing in an orderly manner a white dentifrice and a colored dentifrice or by mixing differently colored dental products, either as the tube is filled or as the dentifrice is dispensed.

The importance of fluoride treatments for hardening tooth enamel and fighting tooth decay has been recognized almost universally within recent years and dentifrice compositions containing fluorides have been marketed and have been found to be effective components of treatments to inhibit tooth decay. Yet, the effectiveness of soluble fluorine-containing compounds, such as sodium monofluorophosphate and sodium fluoride or mixtures thereof, has been limited by the reactivity of such compounds with other components of normal dentifrice compositions, such as calcium or other alkaline earth or heavy metal compounds, especially those which are soluble in the medium, e.g., water, employed. Even essentially insoluble (usually water insoluble) salts, such as calcium phosphates, and other polishing agents, can adversely chemically react with the mentioned fluorine-containing compounds. Additionally, various dentifrice components, such as quaternary ammonium salt bactericides, soluble aluminum and zinc salts (which act as astringents), mild acids or acid-forming materials for producing gradual pH changes in the mouth during tooth brushing and effervescent or bubble-releasing materials, often have to be omitted from dentifrice formulations due to undesirable reactions thereof with other dentifrice components during storage. Accordingly, there has been a need for dentifrice compositions in which reactive materials may be included and which do not undergo objectionable prior reactions during storage. Thus for example, important improvements in utility would result if one were able to employ normally reactive components in a dentifrice composition that could be dispensed together readily from an economical single container. Such a dentifrice is an embodiment of the present invention.

In accordance with this invention a stabilized packaged dentifrice comprises at least two components which are normally reactive with each other and which are maintained separated from each other in a dispensing container from which they are dispensable together through a closable opening therein. Preferably, each of the two mentioned components is in a separate portion of the dentifrice, held apart from the other portion in a dispensing container, with a relatively small interface between the portions and with such portions being divided at such interface by a separating material, which may also be extrudable. The dentifrice extruded is preferably homogeneous in appearance (although really composed of separate material "streams"). It is usually of one color and that color is preferably white.

Figure 1:
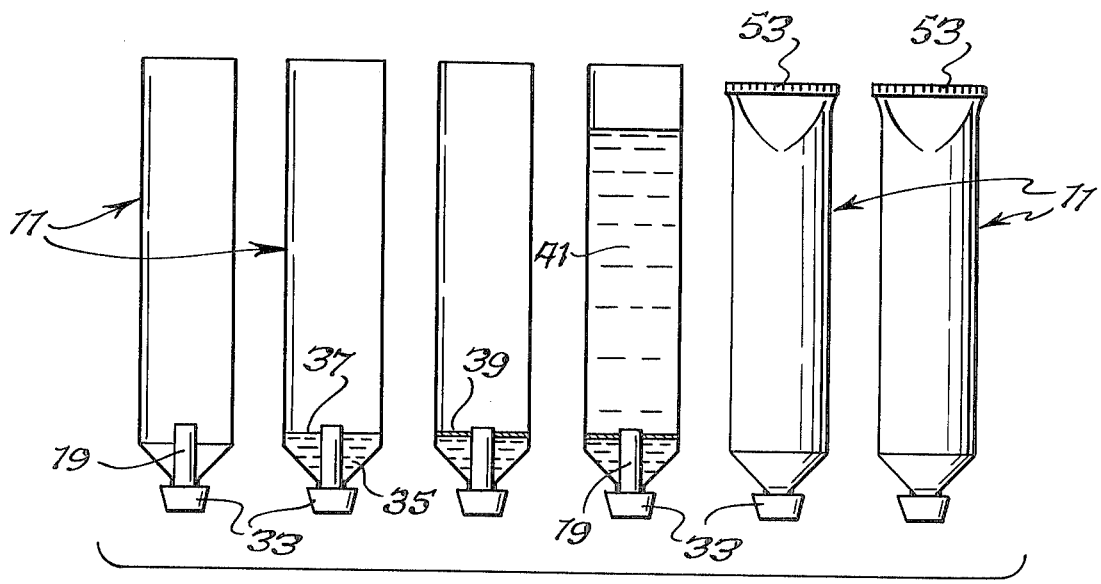
Figure 1:
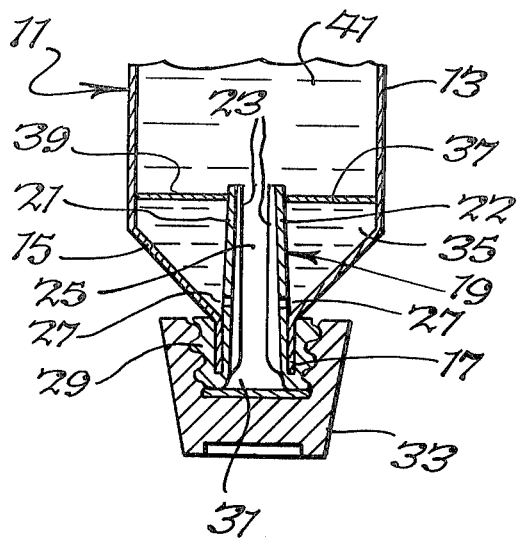
Figure 3:
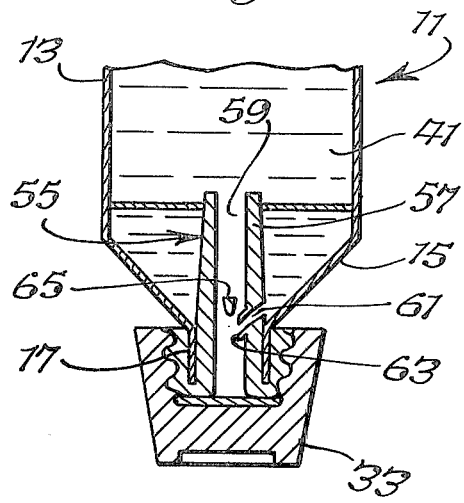

The invention will be readily understood by reference to the preceding and the following description, taken in conjunction with the drawing in which:

FIG. 1 is vertical central sectional elevation of a dispensing end of a tube of the present stabilized packaged dentifrice;

FIG. 2 is a vertical sectional elevation of the manufacture of the present stabilized packaged dentifrice, showing the filling of reactive dentifrice portions into dispensing tubes containing blending means; and FIG. 3 is a central vertical elevation of a modification of the product of FIG. 1, showing the addition of a reactive dentifrice portion to the interior of a ribbon of dentifrice being dispensed.

Collapsible dispensing tube 11 has a side wall 13 and a shoulder portion 15 terminating in a neck 17 onto which is pressed and held firmly in place a blending fitting 19, preferably made of synthetic organic polymeric plastic materials, such as nylon or other suitable moldable and form-retaining polymer, preferably of the thermoplastic type. Blending fitting 19 includes a longitudinally extending tubular portion 21, the wall 22 of which is shown tapered and containing internal ribs 23. Wall 22 determines a longitudinal passageway 25. A plurality (usually from 2 to 6 but even single passageways may be employed) of transverse passageways 27, located neare the joinder of the shoulder and neck portions of the tube, passes through wall 22. The blending fitting includes an externally threaded outer portion 29 and a dispensing opening 31, which is a continuation of passageway 25. A sealing cap 33 may be screwed onto threaded portion 29 of the blending fitting to prevent unintentional discharge of contents from tube 11.

As is illustrated in FIG. 1, initially a first portion of dentifrice 35 is filled into the tube, as will be described with reference to FIG. 2, to the level or interface indicated by numeral 37. Preferably then, an "insulating" or protective intermediate layer of non-reactive material 39 is applied and then the second portion of the dentifrice, identified by numeral 41, is filled into the tube while the tube is maintained in inverted position, as illustrated. Upon application of pressure to the tube, streams of the first portion of the dentifrice pass through openings 27 into passageway 25, forming stripes or "inlays" in the surface of the first dentifrice in such passageway. Entry of the first portion into the second portion is facilitated by the presence of the "upstream" ribs 23 and a uniform proportion of first dentifrice portion to second dentifrice portion is obtained. Because of the location of the tranverse openings 27 essentially all of the product can be discharged and the dispensed product is of substantially uniform composition throughout dispensing. Ideally, the portion of dispensing passage 31 "downstream" (upon dispensing) of transverse openings 27 will be as short as is feasible so as to minimize contacting of any reactive portions of the dentifrice with each other during storage for any appreciable time between uses.

In FIG. 2 a plurality of tubes 11 is illustrated passing through stations under various filling and other mechanisms. Thus, at the first station (from the left) there is shown an empty tube, containing blending fitting and cap screwed onto it in sealing engagement, preparatory to filling. At such station the tube may be cleaned of minor particles of dust, etc. by an air blast. At the next station a first filling head 43 is illustrated, communicating with a source 45 of first dentifrice portion to be filled into a tube 11 in response to applied pressure. It will be noted that filling head 43 includes an internal passageway 47 which, in extensions 47a, which form an annular passageway, passes about the "upstream" end of blending fitting 19, thereby preventing any of the first portion of the dentifrice being filled from contacting the upstream end of the blending fitting or of entering passage 25 therein. Filling head 47 is lowered into position about blending fitting 19 and the desired proportion of the first dentifrice portion is inserted into tube 11 in a known manner, as filling head 47 is withdrawn, so that the "height" of the first dentifrice portion is at 37, as indicated. By such operation the entrapment of air is prevented and the possible surface of contact between the first and second dentifrice portions is minimized.

At the third stage of the filling operation, a preferred operation, a thin layer 39 of insulating, protective or buffering material is introduced by a conventional filling head 49, as illustrated or by other suitable means, e.g., spraying means, gravity feed means, a pump, depending on the character of the protective material. For example, in some instances the protective material may be added to the tube or sprayed into place as a liquid or flowable substance and in other cases the filling head may be adapted to spread a thin layer of a thicker material over the "upper" (as illustrated) surface of the first dentifrice portion.

At the fourth stage filling head 51 is utilized to pressure feed the second dentifrice portion into tube 11 to the desired height thereof and at the fifth stage crimping means, not illustrated, crimp the upper end of the tube closed, as at 53. After sealing off of the container it is ready for cartoning, casing, warehousing and shipment.

Although the described product, with external inlaid dentifrice, is completely satisfactory for many uses and may even be preferred sometimes, it is often preferable that the extruded dentifrice should be of a perfectly uniform surface appearance, not exhibiting any evidence of being composed of two different dentifrice portions. In such instances an insert of the type illustrated in FIG. 3 may be employed. The parts shown in FIG. 3 are the same as those of FIG. 1 except for the insert, which shall be described in detail. Insert 55 includes a tubular wall portion 57 defining passageway 59 through which second dentifrice portion 41 is fed by compression of tube 11. A transverse opening 61 or several such openings are so located as to allow the passage of the first portion of dentifrice through the wall and into the interior of the second dentifrice portion flowing through the discharge passageway. As will be seen from the figure, passageway 61 is angled as it passes through wall 57 so as to promote flow of the first dentifrice portion through it and the passageway is extended and turned in the direction of flow at 63 after passing through wall 57. To promote flow of the first dentifrice portion into the interior of the dispensing passageway 59 a tapered obstruction, shroud or similar construction 65 may diminish the volume of the second dentifrice portion flowing as it approaches the outlet of part 63. Such shroud or baffle may be affixed to the interior of wall 57 by any suitable means but preferably is molded into it or fused to it, as is the transverse passageway extension 63.

The material of construction of the tube is preferably aluminum with polymeric plastic cap and blending fitting. The dentifrice and the different portions thereof, the various compositions of which will be described later, will normally be extrudable through the dispensing opening, which will often be 0.4 to 1 cm. in diameter and the dentifrice dispensed will be form retaining, i.e., will not fall through the bristles of a toothbrush on which it is deposited. Because of this characteristic the two reactive dentifrice portions packaged in the dispensing tube or other suitable container will not tend to intermix after packaging. The openings in the dispensing passage wall through which the first dentifrice portion passes usually are of a diameter from one to four millimeters, which diameter will normally be from 0.1 to 0.5 times that of the dispensing passageway. Of course, instead of circular openings openings of other shapes, e.g., triangles, ellipses, arcs, segments, rectangles may also be employed but the cross-sectional areas thereof will usually be equivalent to those previously given for circles of the diameters mentioned.

The number of openings through the dispensing passageway walls will be chosen to regulate the desired proportions of the dentifrices to be discharged. The openings will be located nearer to the dispensing end of the tube wherein the first dentifrice portion is stored before dispensing. Normally such location will be at the end of such storage zone, external to the discharge passageway, or no more than one centimeter, preferably no more than 5 mm., from it. Similarly, the distance from the transverse passageway exit, where the first dentifrice portion contacts the second dentifrice portion, to the end of the dispensing passageway where dentifrice may lie between uses (to where the brush removes it), will be kept small, preferably being no more than one cm., more preferably being less than 0.5 cm.

The first dentifrice portion will usually have an "upper" surface thereof no closer to the inlet opening of the main discharge passageway than about 1 cm. and preferably no more than 5 mm. Such a range of distances may be from 0.3 to 2 cm., preferably from 0.5 to 1 cm. The separating or buffer layer of protective material between the first and the second dentifrice portion will normally be no thicker than 3 mm. and preferably is 1 to 2 mm. thick but may be thicker in some cases, e.g., 1 to 6 mm.

Instead of employing blending fittings of the type shown on collapsible tubes, such fittings may also be used on resilient polyethylene tubes, "aerosol" pressurized gas propelled dentifrice outlet valves, squeeze bottle outlets and on other pressure actuated dispensers. It will be evident to one of skill in the art how the blending fitting may be adapted for installation in such other containers.

Although it is desirable to have a buffer layer of non-reactive material between the first and the second dentifrice portions, in some embodiments of the invention, due to the limited area of the interface between such portions, little reaction will occur and therefore the absence of the buffer may be acceptable. Normally, as in the illustrated embodiments of the invention, the ratio of the interface area to the dentifrice volume in the filled dispensing container will be less than 0.3, preferably less than 0.2, e.g., 0.05 to 0.2. Nevertheless, in some aspects of the invention one may employ mixed dentifrices such as those made by the methods of U.S. Pat. No. 3,881,529 and British Pat. No. 962,757, both incorporated herein by reference, without intervening buffer layers. Of course, when the filling machines of such patents are modified to allow the interposition of a buffer between the layers of dentifrice, lesser interaction will be obtained. Also, when using such dentifrices no special blending fitting is necessary in the dispenser neck.

The dentifrices produced by the dispensing of both chemically reactive portions thereof from a container in which they are maintained substantially separate will be extruded or otherwise discharged from the container as a unitary form-retaining ribbon, of sufficient viscosity or thickness to rest atop normal toothbrush bristles without descending between them. The dentifrice produced and the component portions may be opaque, translucent or transparent or may be mixtures thereof but usually preferably will appear to be of a single color and type. Preferably, only two dentifrice compositions are fused or extruded together but more can be used. For example, a major or second dentifrice portion, identified by numeral 41 in FIG. 1, may be composed of different compositions, each of which may be a longitudinal "block" in the tube, parallel to but separate from other such compositions. Similarly, the minor or first dentifrice portion may be composed of a plurality of different component dentifrice compositions separated from each other. If desired, portions of the dentifrice may include encapsulated materials, especially encapsulated materials which are most chemically reactive with other components of the dentifrice.

Dentifrice compositions normally comprise a vehicle, a polishing agent, a gelling agent and a surface active or detersive agent. Generally, the vehicle is compatible with all other dentifrice constituents although, as when it is aqueous, it may promote reaction between other normally chemically reactive components. However, the polishing agent, which may contain or may produce insolubilizing ions, such as calcium ions, which may react with soluble fluorides to insolubilize them and thereby inactivate them; and detergents, such as anionic detergents, which may react with cationic antibacterial compounds to inactivate them, should be separated from such reactive materials, when possible, to prevent loss of desired effect during manufacture and storage. The usual vehicles of dentifrices are water and lower polyhydric alcohols of 3 to 6 hydroxyl groups and 3 to 6 carbon atoms per molecule. The most preferred humectant vehicles are glycerol and sorbitol, usually in an aqueous medium. Most preferably aqueous glycerol-sorbitol mixtures are employed. When transparent dentifrices are manufactured, with the index of refraction of the polishing agent being approximately the same as that of the vehicle, the proportion of moisture is usually held to a minimum. Instead of the particular polyhydric alcohols previously mentioned other liquid polyols may also be utilized, such as polyethylene glycols, mannitol and other sugar alcohols, and polyoxyethylene alcohols.

The polishing agents are finely divided water insoluble powdered materials of particle sizes such that they pass a 140 mesh screen, U.S. Standard Sieve series and preferably are from 1 to 40 microns in diameter, most preferably 2 to 20 microns, with distributions of particle sizes being normal over such ranges. Examples of such agents are dicalcium phosphate, tricalcium phosphate, insoluble sodium metaphosphate, crystalline silica, colloidal silica, complex aluminosilicates, aluminum hydroxide (including alumina trihydrate), magnesium phosphate, magnesium carbonate, calcium carbonate, calcium pyrophosphate, bentonite, talc, calcium silicate, calcium aluminate, aluminum oxide, aluminum silicate and silica xerogels, all of which have polishing activity but are not objectionably abrasive. With respect to many such compounds the corresponding alkali metal or alkaline earth metal salts are also useful and may be employed, providing they are sufficiently insoluble. Most of the polishing agents mentioned are most useful in the preparation of opaque dentifrices, but some them, such as the colloidal silicas, especially silica xerogels, and complex sodium aluminosilicates, may be used to make clear dentifrices because their indexes of refraction approximate those of the rest of the dentifrice constituents in an appropriate vehicle.

The gelling agents used to make the dentifrices of the present invention are known in the art and include the natural and synthetic gums and gum-like materials, such as alkali metal carboxymethyl cellulose, hydroxyethyl carboxymethyl cellulose, polyvinyl pyrrolidone, Irish moss, gum tragacanth, hydroxypropyl methyl cellulose, methyl cellulose, starches, starch glycolates, polyvinyl alcohol, alginates, carob beam gums, the hydrophilic colloidal carboxyvinyl polymers, such as those sold under the trademarks Carbopol 934 and Carbopol 940, diatomaceous earths, bentonite and other natural clays (these also may function as polishing agents), proteinaceous materials, either animal- or silicated clays sold under the trademarks Laponite CP and Laponite SP. Certain colloidal silicas such as the aerogels, Syloids 244 and 266 and Aerosil, and pyrogenic silica, sold as Cab-O-Sils, may be used also for thickening or gelling properties. Of course, as with the other constituents of the dentifrices, mixtures thereof may be employed to obtain specially desirable properties in the product. Generally, the gelling materials utilized are gellable with water or alkanols, especially with polyhydric alcohols, such as glycerol and sorbitol. Usually the gel is formed with at least some water present.

The synthetic organic detergents or surface active agents which may be employed in the present compositions assist in emulsifying or otherwise dispersing the components of the dentifrice uniformly and add their cleaning action to the product. In some cases they are germicidal and aid in prophylaxis. Although the organic surface active materials used may be anionic, nonionic, ampholytic or cationic, it is generally preferred to employ, at least as the major detersive constituent, either an anionic or a nonionic material, or a mixture thereof, and of these, the anionics are highly superior in most compositions. In addition to their desired surface active, emulsifying and detersive effects, such materials impart to dentifrices good foaming properties. Generally, they will include long chain fatty or poly-lower alkoxy groups, plus hydrophilic radicals. Usually, the anionic detergents will be in the forms of salts, especially water soluble salts of alkali or alkaline earth metals. Among the useful anionic detergent materials may be mentioned the higher fatty acid monoglyceride monosulfates, such as the sodium salts of the monosulfates of monoglycerides of hydrogenated coconut oil fatty acids, higher alkyl sulfates, such as sodium lauryl sulfates, alkyl aryl sulfonates such as sodium linear dodecyl benzene sulfonate, olefin sulfonates, such as sodium higher olefin sulfonate in which the olefin group is of 12 to 20 carbon atoms, higher alkyl sulfoacetates, higher fatty acid esters of 1,2-dihydroxy propane sulfonates, the substantially saturated higher aliphatic acyl amides of lower aliphatic aminocarboxylic acid compounds, such as those having 12 to 16 carbon atoms in the fatty acid, alkyl or acyl radicals, higher alkyl poly-lower alkoxy (of 10 to 100 alkoxies) sulfates, higher fatty acid soaps and the like. In this specification for convenience and ease of presentation, the soluble soaps are considered to be synthetic organic detergents. Examples of the mentioned amides are N-lauroyl sarcosine and the sodium, potassium and ethanolamine salts of N-lauroyl-, N-myristoyl- and N-palmitoyl sarcosine. In the above descriptions, "higher" refers to chain lengths of 12 to 22 carbon atoms, preferably 12 to 18 carbon atoms and most preferably 12 to 16 carbon atoms. Of course, in broader embodiments of the invention sulfuric reaction products which include long chain hydrophobic groups and hydrophilic radicals are also useful and such compounds are well known. See the text *Surface Active Agents*, Vol. II (1958), by Schwartz, Perry and Berch.

Among the nonionic materials which have been found to be useful detergents are those including chains of lower alkylene oxides, e.g., ethylene oxide, propylene oxide, in which there are present from 10 to 100 or more moles of lower alkylene oxide. Among such materials are the block co-polymers of ethylene oxide, propylene oxide and propylene glycol, sold as Pluronics ®, the alkyl phenyl polyethoxy ethanols, sold as Igepals ®, the mixed copolymers of ethylene oxide and propylene oxide, sold as Ucons ®, and various other well known nonionics derived from fatty alcohols or acids and polyethylene oxide. The amphoteric agents and cationics, which may sometimes be present, although usually it will be desirable to avoid the presence of cationic detergents together with anionic materials, include quaternized imidazole derivatives, sold as "Miranols ®, such as Miranol C₂M", and cationic germicides, such as diisobutylphenoxyethoxyethyl ammonium chloride and tertiary amines having a higher fatty alkyl group and two polyoxyethylene groups attached to the nitrogen thereof.

In addition to the mentioned materials various adjuvants and additionally active components may also be present for their desired effects. For example, flavoring materials are important dentifrice components, fluorine-containing compounds are often present for their desirable effects on the teeth, helping to inhibit tooth decay, antibacterial compounds, astringents, protein precipitating agents and effervescing components may be present. Among the flavoring materials employed, in addition to sweetening agents, such as saccharin, are the essential oils but also included are various flavoring aldehydes, esters, alcohols and similar materials known in the art. Examples of the essential oils include those of spearmint, peppermint, wintergreen, sassafras, clove, sage, eucalyptus, lemon and lime. Also useful is methyl salicylate. The fluoride compounds most preferably employed include sodium monofluorophosphate, sodium fluoride and stannous fluoride. Of these, the more soluble sodium salts are most liable to be inactivated by reaction with alkaline earth metal salts and therefore are preferably maintained separate from such salts in the dentifrice composition. For example, in a fluoride dentifrice the formulation will be divided into two parts, substantially all of the ingredients except any chemicals reactive with the fluoride e.g., dicalcium phosphate, tricalcium phosphate, calcium carbonate and any more soluble calcium salts, being concentrated in one of the separate compositions while said calcium-containing compound is in the other with the other dentifrice constituents, each such composition part having none of the other chemically reactive component present. When a cationic bactericide such as a quaternary ammonium bactericide is present in the composition, if it is desired to employ an anionic detergent the cationic and anionic surface active materials will be maintained in separate portions of the dentifrice, which portions are blended together upon dispensing. The quaternary ammonium salts are those in which the anion is usually halogen or sulfate, one or two substituents on the nitrogen are higher alkyl of 10 to 18 carbon atoms and the other substituents are lower alkyl of 1 to 4 carbon atoms or aryl, e.g., phenyl. Among such compounds are cetyltrimethyl ammonium bromide, dibenzyl dimethyl ammonium chloride and benzyl dimethyl stearyl ammonium chloride. If desired, so that the portion containing the cationic compound will have a surface active agent present therein, a nonionic surface active agent may be utilized in it. Similarly, to give body to the portion of the dentifrice containing fluoride or fluorine-containing compound a polishing agent may be present with it that is non-reactive with the fluorine, e.g., silica. Similar considerations govern the use of protein precipitating agents which may be kept separate from proteinaceous gelling materials and other protein-containing compounds in the dentifrice. Also, if effervescent dentifrices are to be made one portion of the effervescent mixture may be kept in each of the dentifrice parts, e.g., sodium bicarbonate in one part and food acid or food acid precursor, e.g., glucono-delta-lactone, in the other part. Such food acid, e.g., citric acid, gluconic acid, malic acid, tartaric acid, may also be used to change the pH of the dentifrice in the mouth as brushing is continued and in some cases it will be desirable to have at least a portion of the acid encapsulated to further promote later acidification during the toothbrushing operation. Of course, other chemically reactive or chemically incompatible pairs of constituents may also be employed, providing that they are separated in accordance with this invention.

The proportions of the various dentifrice components are those normally employed in the manufacture of dentifrices and the specifications for the components are essentially the same. Thus, such materials are described in the textbook, Cosmetics:Science and Technology, by Sagarin, second printing, 1963, published by Interscience Publishers Inc., hereby incorporated by reference. In the manufacture of the usual opaque dental creams there will normally be present 20 to 75% of polishing agent whereas in the manufacture of clear dental gels this percentage may typically be from 5 to 40%. The preferred proportions of such constituents are 40 to 60% and 10 to 30%, respectively. Gelling agent contents will usually be less than 5% and in most instances from 0.1 to 3% will suffice, with a preferred range, especially applicable when sodium carboxymethyl cellulose is the gelling agent, being from 0.3 to 1.5%. The dentifrice vehicle, exclusive of water (some of the water excluded is that normally present with sorbitol), will normally be from 10 to 85% of the product, with from 10 to 35% being a typical range for the production of opaque dentifrices and from 40 to 85% being useful for the manufacture of clear dental preparations. Preferred ranges are, respectively, from 15 to 30%, 35 to 60%, and 50 to 75%, with polyhydric alcohols being preferred as the vehicles. In the most preferred vehicles, in which glycerol is mixed with sorbitol, the glycerol:sorbitol ratio will usually be from 0.3:1 to 10:1 for the opaque products and from 1:5 to 5:1, more preferably 1:3 to 1:1 for the clear dentifrices. Moisture contents of the dentifrices, including moisture normally present in the sorbitol solution employed, will generally range from 5 to 35%, usually being 8 to 30% and preferably 20 to 30% of the opaque dentifrices. For clear dentifrices this range may be from 0 to 30%, preferably 10 to 20% and more preferably 15 to 30%. Surface active agent or detergent content will usually be from 0.5 to 5% of the dentifrice but may be increased to 10% in some instances. In preferred embodiments of the invention the detergent content will be from 1 to 3%. When nonionic detergents are employed their content will normally not be outside the range of 0.1 to 3% and will preferably be from 0.5 to 2%. Adjuvants, exclusive of flavorings and solvents, will normally be from 0.1 to 10%, preferably being from 0.2 to 5%. Flavoring will generally constitute from 0.5 to 2.5 percent of the dentifrice and solvent content may be 0 to 10% and, if present, is preferably 1 to 5%, e.g., 2% of chloroform or equivalent. The adjuvants include tooth treating (hardening) chemicals such as fluorides; antibacterial agents; components of effervescing reaction mixtures; protein precipitation agents; pH regulators; and astringents. Such materials and other adjuvants, such as coloring and whitening agents, preservatives, silicones, chlorophylls, ammoniated compounds, lubricants, etc., are described in detail in U.S. Pat. No. 3,840,657 (Norfleet), as are other dentifrice components and formulations. Said patent is hereby incorporated by reference.

The dentifrice component parts may be made by standard manufacturing methods before being filled into the dispensing containers by any of the techniques previously described. Thus, as in U.S. Pat. No. 3,711,604 and 3,840,657, the dentifrice may be degassed during manufacture, or gas bubbles may be intentionally added to it.

When two separate dentifrice portions are employed, each containing a component reactable with another and separate component of the composition, one portion may comprise from 2 to 50% of the dentifrice and a second portion may be from 98 to 50% thereof (excluding in such calculations any intervening separating dentifrice or other materials such as a gel made from a dentifrice binder, vehicle and water). Preferably such ranges will be from 5 to 20% and 95 to 80%. The intervening material may be a gel as described or may be a complete dentifrice except for the two reactive components. The proportion thereof will usually be from 0.5 to 5% of the dentifrice, by weight.

The compositions of the separate dentifrice portions will be modified in each case according to the final formulation desired. Thus, when a soluble fluoride, such as sodium fluoride or sodium monofluorophosphate or a mixture thereof, is present, in a percentage which will normally be from 0.02 to 3%, preferably 0.3 to 2%, it will be in a portion of the dentifrice, preferably the first portion thereof, without any reactive insolubilizing material being present therein, such as dicalcium phosphate or other reactive alkaline earth metal salt. Similarly, when an astringent salt is present such as aluminum chloride or zinc sulfate, these will be maintained separate from fluorine-containing compounds and anionic detergents. Cationic antibacterials and various other antibacterial compounds will be kept separate from reactive materials, such as anionic detergents. Protein precipitating agents, such as aluminum salts will be separated from proteinaceous binders. Acids and bases will be maintained apart. Of course, materials that react to produce a gas, such as carbon dioxide, will be kept separate from each other until they are mixed on dispensing. The proportions of antibacterial compound, astringent, protein precipitant, acid (or base) and effervescing "mixture" will usually be in the range of 0.1 to 2%, 0.2 to 1%, 0.1 to 1%, 0.2 to 2% and 0.3 to 3%, respectively. Of course, various mixtures of such materials may be employed too but care should be exercised so that interreactive materials are maintained separate before final mixing.

The modification of the separate dentifrice formulas to be kept apart in the dispensing container before actual dispensing may cause the omission of a particular desirable component from one of the portions but it is within the invention to substitute a component having a similar effect but not being objectionably reactive. Thus, silica may be used as a polishing agent or bodying agent in place of a calcium salt in the component containing fluoride tooth hardening agent and nonionic surface active agent may be employed with the cationic antibacterial compound instead of the usual anionic detergent. Of course, when an acidifying agent such as citric acid is employed, in addition to being kept separate from sodium bicarbonate with which it reacts to produce the desired foaming on dispensing, it should be maintained separate from other alkaline materials or compounds with which it might also react, such as calcium carbonate. The sodium bicarbonate may be employed in dentifrice formulations in proportions in excess of the stoichiometric proportions required to produce carbon dioxide bubbles, with the excess being useful as an auxiliary polishing agent and breath sweetener.

The following examples illustrate the invention but should not be considered as limiting it. Unless otherwise mentioned, all parts are by weight and temperatures are ° C.

EXAMPLE 1

|  | Percent |
|---|---|
| Glycerol | 4.5 |
| Sorbitol | 17.5 |
| Sodium carboxymethyl cellulose (7MF, Hercules) | 0.8 |
| Sodium benzoate | 0.5 |
| Sodium saccharin | 0.2 |
| Water | 22.4 |
| Dicalcium phosphate (90% hydrate) | 45.5 |
| Fumed silica (Cab-O-Sil M5) | 5.0 |
| Sodium lauryl sulfate | 1.5 |
| Sodium fluoride | 0.5 |
| Sodium monofluorophosphate | 1.0 |
| Peppermint flavor | 0.6 |
|  | 100.0 |

The above final formula dentifrice is obtained by making two separate dentifrice compositions in accordance with the present invention and filling them into a dispensing tube of the type shown in FIG. 1 by the method illustrated in FIG. 2. The first composition filled comprises about 12% of the entire formula, including 10% of each of the constituents except the dicalcium phosphate, of which none is present, and includes the entire percentages of silica and the fluorine-containing tooth hardening compounds. Next the second portion of the dentifrice is added, with no separating material between the "layers", which take the positions shown in FIG. 2. The tubes are crimped at the upper ends thereof (really the bottom seals), having been previously (before filling) sealed tight at the cap ends. After storage for six months under normal storage conditions, when the mixed dentifrice is dispensed from the tubes in accordance with the present invention the active content of fluorine-containing hardening agent is significantly greater than that from a control formula wherein the various components are homogeneously mixed together before filling and are dispensed from a conventional collapsible dentifrice tube.

In a modification of the above product the percentages of the various components and dentifrice portions are reduced to 98% thereof and a gel layer, as illustrated in FIG. 2, is placed atop the first (minor) dentifrice portion to separate it from the second portion. The gel layer constitutes 2% of the final dentifrice product and is composed of 5% of sodium carboxymethyl cellulose in 95% of a glycerol — sorbitol — water mix like that in the 98% of the dentifrice. In such case the first and second dentifrice portions at the interface show little interaction, compared to the interface of the prior described product of this example and consequently the activity of the tooth hardening fluoride components is increased. In a further modification of the described product the fitment illustrated in FIG. 3 is employed, so that the first portion of dentifrice, rather than forming "invisible stripes" about the circumference of the extruded major dentifrice portion, is extruded through the middle of such portion, where it is even less visible. Such is done with the described compositions with and without intervening extrudable "insulating" layers between the dentifrice portions. Of course, since the storage conditions for such product are essentially the same as those of the products previously described, the fluorine compound stabilities are essentially the same, too.

In still another modification of this example instead of employing the sodium carboxymethyl cellulose gel intermediate the two dentifrice portions in the collapsible dispensing tube, 2% of dentifrice formula containing no dicalcium phosphate (silica is substituted for it) and containing no fluorine-containing compounds is employed as the separating agent. The stabilities of the fluorine-containing compounds in the final dentifrice are thereby preserved better than in homogeneous products.

In all the experiments described the sizes of the dispensing orifices and the fitment orifices and the numbers of such fitment orifices are controlled so that a constant composition of product will be dispensed and both portions thereof will be consumed proportionately, maintaining the final dentifrice compositions substantially constant during its entire use. Thus, to effect this with 12% of the minor component and 88% of the major component of the dentifrice, omitting any separating composition, one may employ a tube outlet having a diameter of about 0.8 cm. and a fitment having six openings, each of 0.1 mm. Of course, allowances will be made in the choices of orifices to compensate for different viscosities of the dentifrice components. Also, the various other tube characteristics, proportions and other conditions are those described in the specification, with the averages of the preferred ranges being used.

EXAMPLE 2

The formulation of Example 1 is modified to include a 50:50 mixture of glycerol and sorbitol in place of the 20:80 mix, Irish moss in place of sodium CMC, a mixture of hydrated dicalcium phosphate and tricalcium phosphate (50:50) in place of the dicalcium phosphate (90% hydrate), sodium N-lauroyl sarcosinate in place of sodium lauryl sulfate and sodium monofluorophosphate in place of sodium fluoride. Different flavors are employed in place of peppermint flavor, e.g., spearmint, clove. The products resulting are of essentially the same tooth hardening characteristics as those of Example 1, after a comparable storage period. They may be made by similar methods, conveniently at room temperature, using automatic filling equipment such as that illustrated in FIG. 2.

EXAMPLE 3

The products of Examples 1 and 2 are made by the method of U.S. Pat. No. 3,881,529 so that the dentifrice parts are separately located in the dispensing tube during storage but are longitudinally situated, as in a plurality of stripes in a matrix or a body of the major proportion of the material. Such product is not as stable on storage as those previously described but is more stable than a homogeneous product including the same components.

EXAMPLE 4

The formulas of Examples 1–3 are modified to include in the minor portion 0.4% of cetyltrimethyl ammonium bromide, together with all the dentifrice constituents except the anionic detergent, and the sodium fluoride and sodium monofluorophosphate are omitted. In place of the sodium lauryl sulfate, 1.3% of which is present in the major portion of the dentifrice, 0.2% of nonionic detergent (polyoxyethanol, Neodol ® 45-11) is used in the minor portion. The proportion of vehicle is increased therein to compensate for the absence of the fluorine compounds. After six months storage of the products made their stabilities are superior to those of comparable homogeneous products.

EXAMPLE 5

Examples 1–3 are repeated with 1.5% of citric acid replacing the fluoride and monofluorophosphate and despite storage for six months the acidification effects of the acid are apparent on use. On the other hand, in a control composition the acid is almost entirely consumed in neutralizing the dicalcium phosphate, converting a substantial proportion to monocalcium phosphate, on storage. Similar effects are obtained when other food acids, such as tartaric and malic acid, are employed, instead of citric acid, and when other "alkaline" polishing agent salts are used.

EXAMPLE 6

The experiments of Examples 1–3 are repeated with an effervescent "mixture" being employed, the sodium bicarbonate (1%) thereof being with the major portion of the dentifrice and 1% of citric acid being with the minor portion, again with the fluorine-containing compounds being omitted. The product expands on dispensing, due to reaction of the two components, despite storage for six months. A control homogeneous product reacts prematurely and causes undesirable swelling of the container and excessive speed of dispensing when the container cap is removed.

In a like manner protein precipitating compounds are included in the formulations, being kept separate from any proteinaceous gelling materials with which they might be reacted.

The products made, as described in the above examples, are all opaque white and exhibit no tell-tale stripes. They are readily manufactured and after lengthy storage periods are still active. However, if desired, colorants may also be employed by including them in one or the other or both portions of the composition to be dispensed. Also, when desired, clear dentifrices are made by following the procedures of the above examples but substituting for the initial dentifrice base composition compositions of Examples 1 and 2 of U.S. Pat. No. 3,840,657. In such cases, the differences between the two "phases" may be minimized or may be accentuated by using transparent coloring materials, too. Of course, in transparent dental gels different polishing agents are employed and opaque constituents are avoided.

EXAMPLE 7

The experiments of Examples 1-6 are repeated with dispensing of the dentifrice being from a pressurized dispenser commonly referred to as an aerosol can, pressurized with nitrogen at 5 to 10 kg./sq. cm. The dispensed product, released upon depressing of a dispensing spout, which depresses a valve button and opens a passageway for dispensing, has the properties of the tube-dispensed products previously described. Before pressurizing, the container may also be filled by either the method illustrated in FIG. 2 hereof or that of U.S. Pat. No. 3,881,529. The pressurized container should be held inverted, with the dispensing valve at the bottom thereof, for normal use and employment of a dip tube is usually avoided due to possible reaction of the components in the tube after mixing and before dispensing. However, the tube design can be modified to all use thereof under some circumstances.

The various proportions recited for the various constituents and dentifrice portions may be modified, usually to a limit of ±20%, without appreciable change in the properties of the products resulting. Also, there may be substituted for the various components others previously described in the specification and the same general effects, desired increased activities of reactive components and improved appearances, will result.

The instant invention is equally applicable to a dentifrice remineralizing demineralized tooth enamel using clacium as phosphate ions from a tube adapted for simultaneous delivery, such as for the example the dentifrices described in German Offenlegungsschrift No. 2452969 the disclosure of which is incorporated herein by reference.

The invention has been described with respect to various examples thereof but is not to be limited to these or the illustrations or descriptions given because it will be evident that one may substitute equivalents for materials, elements or process steps without going outside the scope of the invention described.

What is claimed is:

1. A stabilized dentifrice comprising two paste or gel dentifrice portions, both of which are extrudable from a collapsible dentifrice tube and each of which includes a component which is chemically reactive with the other said component in the other portion, which dentifrice portions are maintained separate from each other by an intervening separating composition which is unreactive with the reactive components of said portions and which is extrudable with one or both of them through an opening in the collapsible dentifrice tube, in a dispensing container from which said portions are dispensable together through a closable opening therein in response to pressure, the first portion being from 2 to 50% of the dentifrice and the second portion being from 98 to 50% thereof, one portion including an alkali metal fluorine-containing salt and the other including a water-insoluble alkaline earth metal salt which is chemically reactive with said fluorine-containing salt and which inactivates such salt and decreases its utility as a tooth enamel hardening agent when stored in contact with it in a homogeneous dentifrice formulation of the same composition as the present dentifrice when dispensed.

2. A stabilized dentifrice according to claim 1 wherein the alkali metal fluorine-containing salt is selected from the group consisting of sodium fluoride and sodium monofluorophosphate and the alkaline earth metal salt is selected from the group consisting of dicalcium phosphate, tricalcium phosphate and calcium carbonate.

3. A stabilized dentifrice according to claim 2 wherein the separating material is a gel layer.

4. A stabilized dentifrice according to claim 3 wherein the first portion is from about 5 to 20% of the dentifrice, the second portion is from about 95 to 80% of the dentifrice, the first portion includes the alkali metal fluorine-containing salt, the second portion includes the alkaline earth metal salt and the separating layer is about 2% of a sodium carboxymethyl cellulose-glycerol-sorbitol-water gel.

5. A stabilized dentifrice according to claim 4 wherein the compositions of the first and second portions are essentially the same with the exception that the first portion includes no such alkaline earth metal salt and the second portion includes no such fluorine-containing salt.

6. A stabilized dentifrice according to claim 5 wherein both portions of the dentifrice and the dispensed dentifrice are of about the same color.

7. A stabilized dentifrice according to claim 6 comprising about 4.5% of glycerol, about 17.5% of sorbitol, about 0.8% of sodium carboxymethyl cellulose, about 45.5% of about 90% hydrated dicalcium phosphate, about 5% of fumed silica, about 1.5% of sodium lauryl sulfate, about 0.5% of sodium fluoride, about 1% of sodium monofluorophosphate, about 22.4% of water and about 1.3% of adjuvants.

8. A stabilized dentifrice according to claim 1 wherein the separating composition is that of the stabilized dentifrice less the reactive components thereof.

* * * * *